United States Patent
Brahem et al.

(10) Patent No.: US 12,196,730 B2
(45) Date of Patent: Jan. 14, 2025

(54) GAS SENSOR DEVICE FOR DETECTING GASES WITH LARGE MOLECULES

(71) Applicants: STMICROELECTRONICS S.r.l., Agrate Brianza (IT); STMICROELECTRONICS PTE LTD, Singapore (SG)

(72) Inventors: Malek Brahem, Singapore (SG); Hatem Majeri, Aix en Provence (FR); Olivier Le Neel, Saint Martin d Uriage (FR); Ravi Shankar, Singapore (SG); Enrico Rosario Alessi, Catania (IT); Pasquale Biancolillo, Pedara (IT)

(73) Assignees: STMICROELECTRONICS S.r.l., Agrate Brianza (IT); STMICROELECTRONICS PTE LTD, Singapore (SG)

( * ) Notice: Subject to any disclaimer, the term of this patent is extended or adjusted under 35 U.S.C. 154(b) by 0 days.

(21) Appl. No.: 18/485,072

(22) Filed: Oct. 11, 2023

(65) Prior Publication Data
US 2024/0036019 A1 Feb. 1, 2024

Related U.S. Application Data

(62) Division of application No. 17/166,580, filed on Feb. 3, 2021, now Pat. No. 11,821,884, which is a division
(Continued)

(51) Int. Cl.
*G01N 33/00* (2006.01)
*G01N 27/02* (2006.01)
*G01N 27/12* (2006.01)

(52) U.S. Cl.
CPC ....... *G01N 33/0047* (2013.01); *G01N 27/021* (2013.01); *G01N 27/12* (2013.01)

(58) Field of Classification Search
CPC ... G01N 33/0047; G01N 27/021; G01N 27/12
See application file for complete search history.

(56) References Cited

U.S. PATENT DOCUMENTS

| 7,359,802 B1 | 4/2008 | Lewis et al. |
| 10,942,157 B2 * | 3/2021 | Brahem ............... G01N 27/021 |

(Continued)

FOREIGN PATENT DOCUMENTS

| CN | 1495424 A | 5/2004 |
| CN | 1618014 A | 5/2005 |

(Continued)

OTHER PUBLICATIONS

California Office of Environmental Health Hazard Assessment, "Cyclosiloxanes," *Meeting of the California Environmental Contaminant Biomonitoring Program Scientific Guidance Panel*, Dec. 4-5, 2008, 12 pages.

(Continued)

*Primary Examiner* — Brian J. Sines
(74) *Attorney, Agent, or Firm* — Seed IP Law Group LLP (57) ABSTRACT

The present disclosure is directed to a gas sensor device that detects gases with large molecules (e.g., a gas with a molecular weight between 150 g/mol and 450 g/mol), such as siloxanes. The gas sensor device includes a thin film gas sensor and a bulk film gas sensor. The thin film gas sensor and the bulk film gas sensor each include a semiconductor metal oxide (SMO) film, a heater, and a temperature sensor. The SMO film of the thin film gas sensor is an thin film (e.g., between 90 nanometers and 110 nanometers thick), and the SMO film of the bulk film gas sensor is an thick film (e.g., between 5 micrometers and 20 micrometers thick). The gas sensor device detects gases with large molecules based on a variation between resistances of the SMO thin film and the SMO thick film.

20 Claims, 10 Drawing Sheets

Related U.S. Application Data of application No. 15/901,721, filed on Feb. 21, 2018, now Pat. No. 10,942,157.

(56) References Cited

U.S. PATENT DOCUMENTS

| | | | |
|---|---|---|---|
| 11,821,884 B2* | 11/2023 | Brahem | G01N 27/021 |
| 2002/0142477 A1 | 10/2002 | Lewis et al. | |
| 2009/0159445 A1 | 6/2009 | Krishna et al. | |
| 2012/0042713 A1 | 2/2012 | Kim et al. | |
| 2016/0018356 A1 | 1/2016 | Shankar et al. | |
| 2017/0016866 A1 | 1/2017 | Chey et al. | |

FOREIGN PATENT DOCUMENTS

| | | |
|---|---|---|
| CN | 1684285 A | 10/2005 |
| CN | 1715900 A | 1/2006 |
| CN | 1788196 A | 6/2006 |
| CN | 104034759 A | 9/2014 |
| CN | 107632044 A | 1/2018 |
| JP | H0486550 A | 3/1992 |
| KR | 20090029681 A | 3/2009 |
| WO | WO 9934199 A1 | 7/1999 |

OTHER PUBLICATIONS

Environment Canada & Health Canada, "Screening Assessment for the Challenge; Dodecamethylcyclohexasiloxane (D6)," Chemical Abstracts Service Registry No. 540-97-6, Nov. 2008, 83 pages.

Environment Canada & Health Canada, "Screening Assessment for the Challenge; Octamethylcyclotetrasiloxane (D4)," Chemical Abstracts Service Registry No. 556-67-2, Nov. 2008, 90 pages.

European Commission. "Regulation (EC) No. 1272/2008 of the European Parliament and of the Council," *Official Journal of the European Union L 353*, Dec. 31, 2008, 1355 pages.

Tropis, "Analysis and Performance Optimization of a gas sensor based on SnO2 nanoparticulate: Application to the detection of CO and CO2," Doctoral Thesis, University of Toulouse, Toulouse, France, Feb. 25, 2010, 264 pages.

\* cited by examiner

GAS SENSOR DEVICE FOR DETECTING GASES WITH LARGE MOLECULES

BACKGROUND

Technical Field

The present disclosure is directed to a gas sensor device to detect air quality.

Description of the Related Art

Air quality is important to maintain one's health. Air pollution may lead to a variety of health issues, such as cardiopulmonary ailments. Children are particularly susceptible to air pollution. Unfortunately, air pollution is not limited to outdoor pollution. A large range of chemical compounds can be found in indoor environments, such as in homes, offices, and factories. For example, large concentrations of volatile organic compounds (VOC) and siloxanes are often detected in indoor environments.

VOCs include compounds such as ethanol, toluene, benzene, formaldehyde, tetrachloroethene (TCE), and methylene chloride. VOCs may derive from a wide variety of different sources. For example, VOCs may derive from air conditioners, building materials, furniture, solvents, paint, and carpeting. VOCs may even be caused by quotidian activities, such a breathing, cooking, and cleaning.

Siloxanes include compounds such as cyclotrisiloxane (also known as D3), cyclotetrasiloxane (also known as D4), cyclopentasiloxane (also known as D5), and cyclohexasiloxane (also known as D6), and hexamethyldisiloxane (also known as HDMS). Siloxanes are generally both toxic and persistent. For example, cyclotetrasiloxane (D4) has been categorized as a disruptor in some countries, and is a potentially reproductive toxicant that can alter human fertility. Cyclotetrasiloxane (D4) has also been shown to interfere with human hormonal functions. As another example, exposure to high doses of cyclopentasiloxane (D5) has been shown to cause uterine tumors and damage the immune and reproductive systems. Cyclopentasiloxane (D5) may also affect the neurotransmitters of the nervous system. Siloxanes have also been shown to have a potential for bioaccumulation in aquatic organisms. Siloxanes may derive from variety of everyday products, such as cosmetics and household cleaners. For example, hair products often include siloxanes to dry faster, and deodorants often include siloxanes to improve application on a human body. Detergents and phone covers also often include siloxanes for its elastomeric properties.

Figure 1:
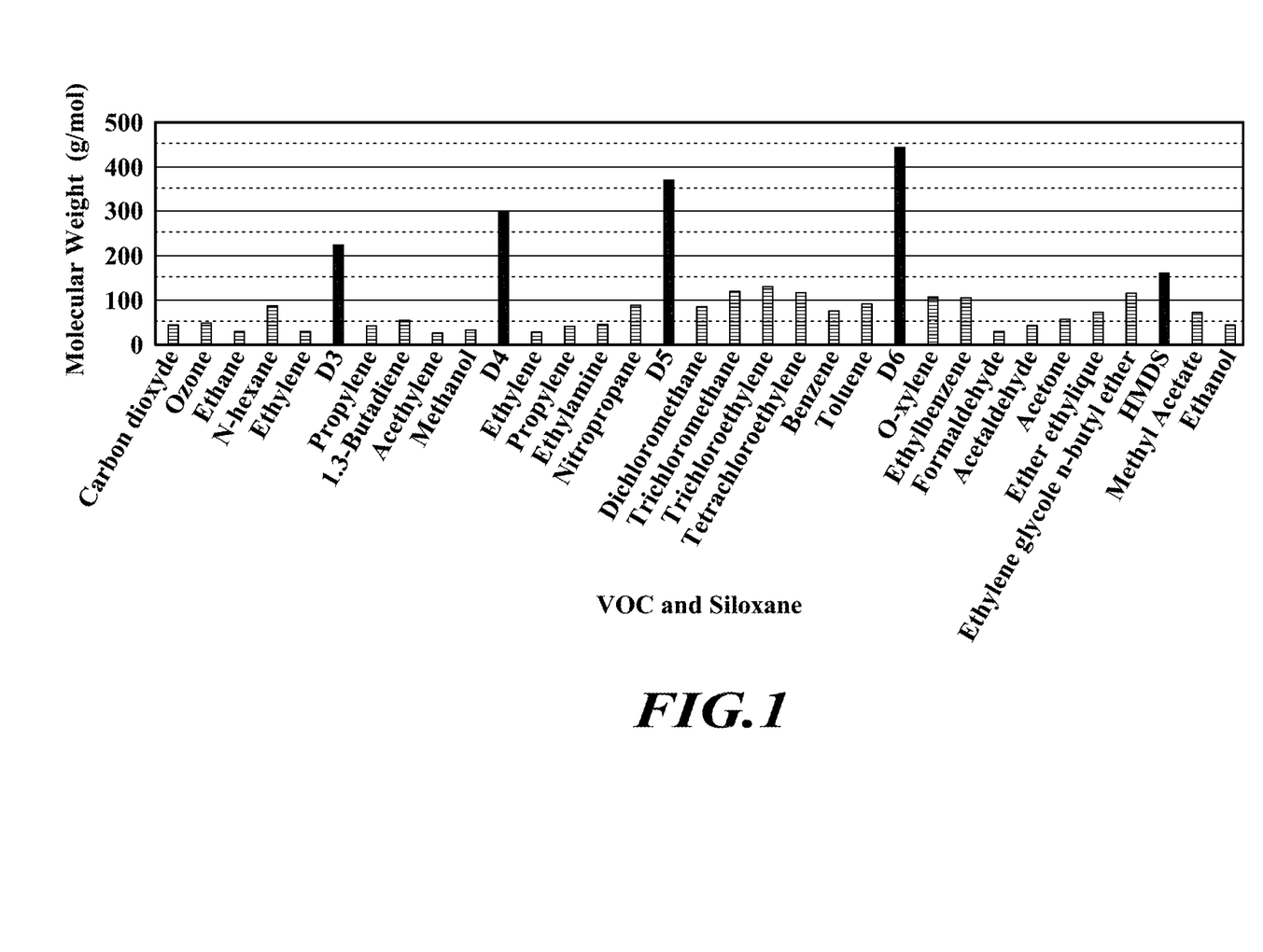
FIG. 1 is a chart showing the molecular weights for a variety of volatile organic compounds (VOC) and siloxanes according to an embodiment of the present disclosure.

Siloxane molecules are large relative to VOC molecules. Siloxane molecules are up to eight times larger than volatile organic compounds (VOC) molecules. FIG. 1 is a chart showing the molecular weights for a variety of volatile organic compounds (VOC) and siloxanes. As shown in FIG. 1, the molecular weights of siloxanes, such as cyclotrisiloxane (D3), cyclotetrasiloxane (D4), cyclopentasiloxane (D5), cyclohexasiloxane (D6), and hexamethyldisiloxane (HDMS) are much larger than the VOCs. For example, ethanol has a molecular weight of 46.068 g/mol, while cyclopentasiloxane (D5) has a molecular weight of 370.8 g/mol.

Some people are particularly sensitive to gases, such as VOCs and siloxanes, and will experience allergic reactions, including headaches, dizziness, and irritation. However, most people are unable to detect hazardous levels of gases. Accordingly, it is important for buildings to be equipped with gas sensors to detect harmful levels of gases. Unfortunately, due to the size of siloxane molecules, siloxanes are not easily detected with known gas sensors. Many gas sensors are insensitive to siloxanes, become instable when exposed to siloxanes, and/or provide inaccurate measurements.

BRIEF SUMMARY

The present disclosure is directed to a gas sensor device that detects gases with large molecules (e.g., a molecular weight between 150 g/mol and 450 g/mol), such as siloxanes. The gas sensor device may be used for a variety of applications, such as an indoor air quality sensor and an outdoor air quality sensor.

The gas sensor device includes a thin film gas sensor and a bulk film gas sensor. The thin film gas sensor and the bulk film gas sensor each include a semiconductor metal oxide (SMO) film, a heater, and a temperature sensor. The SMO film of the thin film gas sensor is a thin film (e.g., between 90 nanometers and 110 nanometers thick), and the SMO film of the bulk film gas sensor is a thick film (e.g., between 5 micrometers and 20 micrometers thick).

Due to the differences between the SMO thin film and the SMO thick film (e.g., the SMO thin film being non-porous and the SMO thick film being porous), the SMO thin film and the SMO thick film react differently to gases with large molecules. In particular, the SMO thin film will undergo very little, if any, change in resistance when exposed to a gas with large molecules, and the SMO thick film will undergo a significant change in resistance when exposed to a gas with large molecules. The gas sensor device detects gases with large molecules, such as siloxanes, based on a variation between the resistances of the SMO thin film and the SMO thick film.

The gas sensor device is also used to selectively detect gases that does not have large molecules (e.g., a gas with a molecular weight that is less than 100 g/mol), such as VOCs. The gas sensor device detects a particular gas based on a lack of variation between the resistances of the SMO thin film and the SMO thick film.

BRIEF DESCRIPTION OF THE SEVERAL VIEWS OF THE DRAWINGS

In the drawings, identical reference numbers identify similar features or elements. The size and relative positions of features in the drawings are not necessarily drawn to scale.

DETAILED DESCRIPTION

In the following description, certain specific details are set forth in order to provide a thorough understanding of various aspects of the disclosed subject matter. However, the disclosed subject matter may be practiced without these specific details. In some instances, well-known structures and methods of manufacturing electronic devices have not been described in detail to avoid obscuring the descriptions of other aspects of the present disclosure.

Unless the context requires otherwise, throughout the specification and claims that follow, the word "comprise" and variations thereof, such as "comprises" and "comprising," are to be construed in an open, inclusive sense, that is, as "including, but not limited to."

Reference throughout the specification to "one embodiment" or "an embodiment" means that a particular feature, structure, or characteristic described in connection with the embodiment is included in at least one embodiment. Thus, the appearance of the phrases "in one embodiment" or "in an embodiment" in various places throughout the specification are not necessarily all referring to the same aspect. Furthermore, the particular features, structures, or characteristics may be combined in any suitable manner in one or more aspects of the present disclosure.

Reference throughout the specification to integrated circuits is generally intended to include integrated circuit components built on semiconducting or glass substrates, whether or not the components are coupled together into a circuit or able to be interconnected. Throughout the specification, the term "layer" is used in its broadest sense to include a thin film, a cap, or the like, and one layer may be composed of multiple sub-layers.

The present disclosure is directed to a gas sensor device that detects gases with large molecules (e.g., a gas with a molecular weight between 150 g/mol and 450 g/mol), such as siloxanes.

Figure 2:
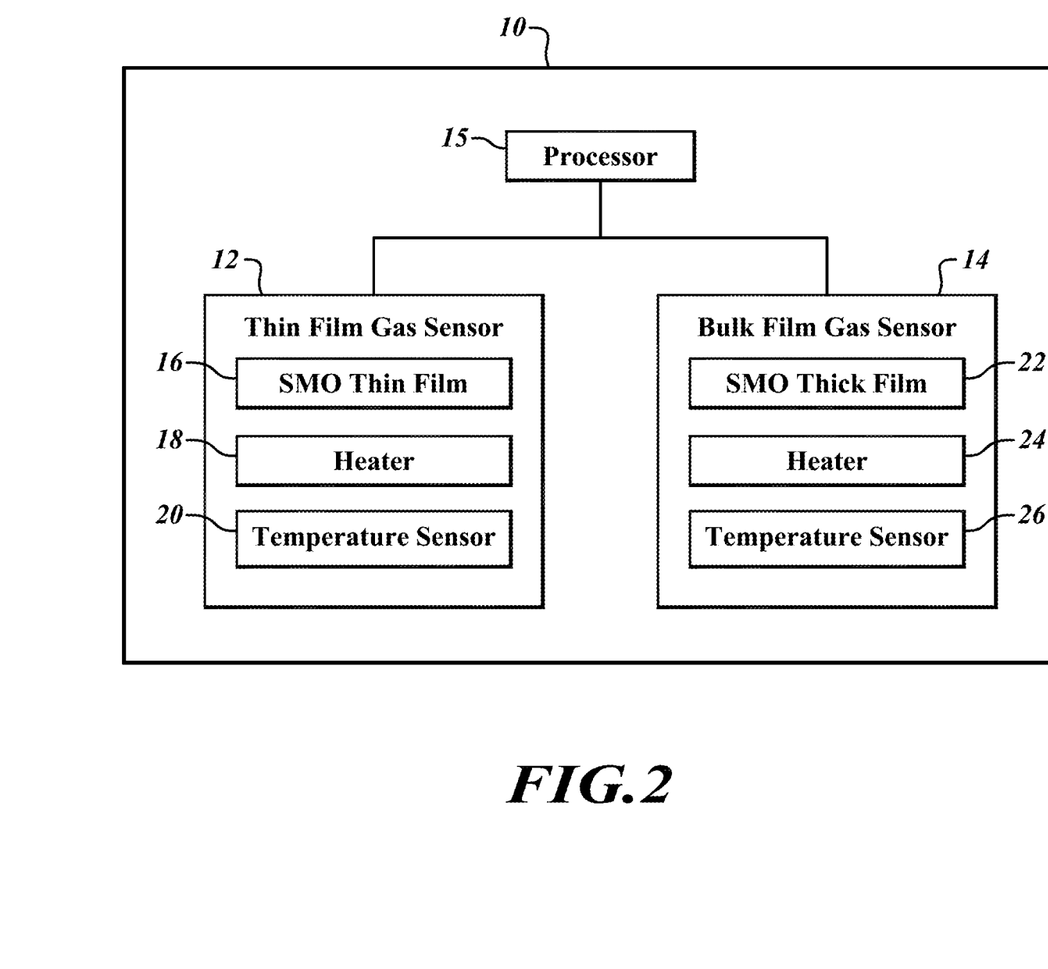
FIG. 2 is a block diagram of a gas sensor device according to an embodiment of the present disclosure.

FIG. 2 is a block diagram of a gas sensor device 10 according to an embodiment of the present disclosure. The gas sensor device 10 detects gases with large molecules, such as siloxanes. The gas sensor device 10 includes a thin film gas sensor 12, a bulk film gas sensor 14, and a processor 15.

The thin film gas sensor 12 and the bulk film gas sensor 14 each includes a thin film that is an active sensor area, a heater, and a temperature sensor. The thin film gas sensor 12 includes such as a semiconductor metal oxide (SMO) film 16, a heater 18, and a temperature sensor 20. The bulk film gas sensor 14 includes an SMO thick film 22, a heater 24, and a temperature sensor 26. Throughout this disclosure the films are referred to as SMO films, however other active sensor materials may be used as the sensor films.

The SMO thin film 16 and the SMO thick film 22 are made of a material that chemically reacts with gases, such as VOCs, in a surrounding environment. For example, the SMO films may include tin oxide ($SnO_2$), zinc oxide ($ZnO_2$), and/or indium oxide ($In_2O_3$). The SMO films act as active sensor areas. When heated to certain temperatures, the SMO films experience a change in resistivity when exposed to certain gases. For example, when heated to between 100 degrees Celsius and 400 degrees Celsius, a resistance of a film of tin oxide changes in the presence of methane gas ($CH_4$), liquid petroleum gas (LPG), or hydrogen gas ($H_2$). Accordingly, a presence of a specific gas may be detected based on a current resistivity of the SMO films. As previously discussed, although the SMO thin film 16 and the SMO thick film 22 are referred to as SMO films throughout this disclosure, other active sensor materials that are sensitive to gases may be used.

In one embodiment, the materials for the SMO thin film 16 and the SMO thick film 22 are selected such that the SMO thin film 16 and the SMO thick film 22 have the same resistance and sensitivity to gases, such as VOCs. For example, in one embodiment, the SMO thin film 16 and the SMO thick film 22 are made of the same material and are heated to the same temperature. It is noted, however, that different material and temperatures for the SMO thin film 16 and the SMO thick film 22 may be used.

Figure 3:
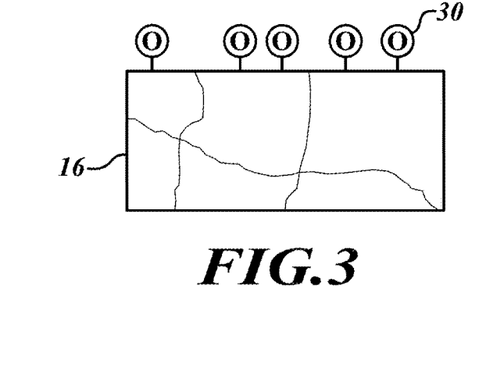
FIG. 3 is a cross-sectional view of a semiconductor metal oxide (SMO) thin film reacting with gas molecules according to an embodiment of the present disclosure.

The SMO thin film 16 is a thin film. The SMO thin film 16 may, for example, be between 90 nanometers and 110 nanometers thick. Generally, SMO thin films are non-porous, and do not include any spaces or cavities. FIG. 3 is a cross-sectional view of the SMO thin film 16 reacting with gas molecules 30 according to an embodiment of the present disclosure. As the SMO thin film 16 is non-porous, the SMO thin film 16 may include some cracks, but does not include any spaces for gas molecules 30 to pass through. As a result, the gas molecules 30 react with (e.g., reduce or oxidize) the SMO thin film 16 at the SMO thin film's 16 exposed upper surface.

Figure 4A:
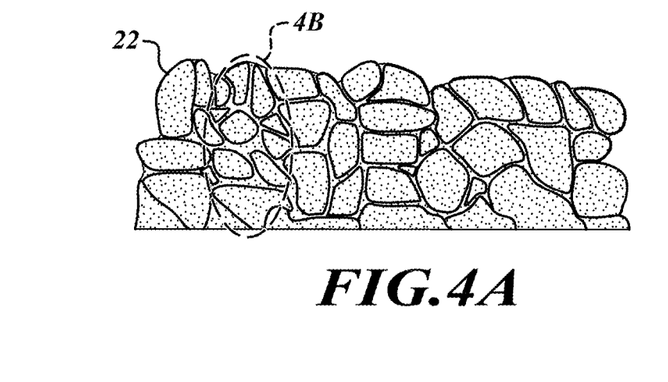
FIGS. 4A and 4B are a cross-sectional view of an SMO thick film reacting with gas molecules according to an embodiment of the present disclosure.
Figure 4B:
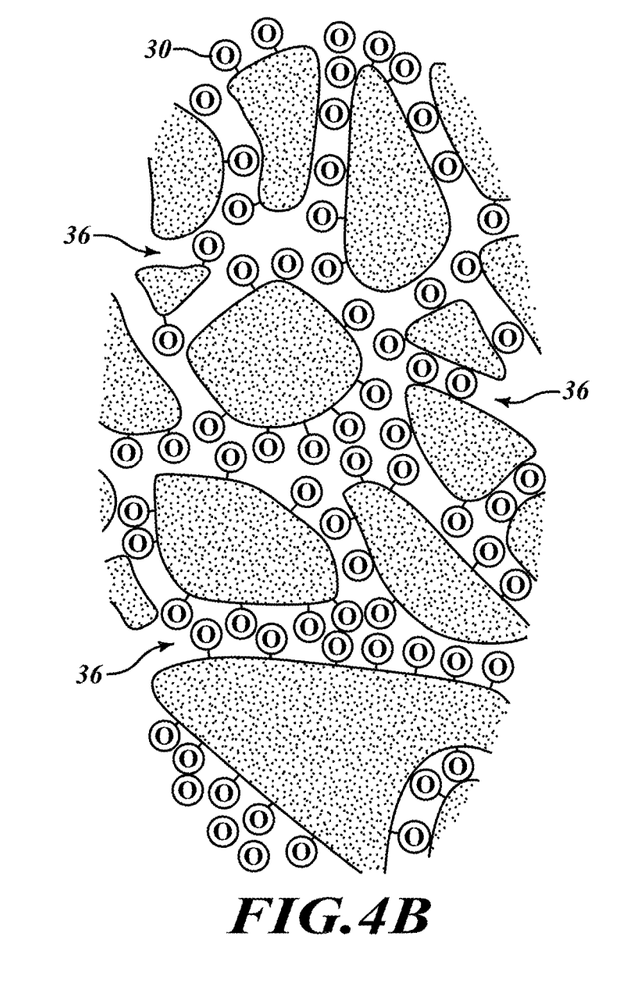

The SMO thick film 22 is a thick film. The SMO thick film 22 may, for example, be between 5 micrometers and 20 micrometers thick. Generally, in contrast to SMO thin films, SMO thick films are porous, and include spaces or cavities. FIGS. 4A and 4B are a cross-sectional view of the SMO thick film 22 reacting with gas molecules 30 according to an embodiment of the present disclosure. As the SMO thick film 22 is porous, the SMO thick film 22 includes spaces 36 for gas molecules 30 to pass through or enter. As a result, the gas molecules 30 react with (e.g., reduce or oxidize) the SMO thick film 22 at the SMO thick film's 22 exposed upper surface, and at surfaces within the spaces 36 of the SMO thick film 22.

Figure 5:
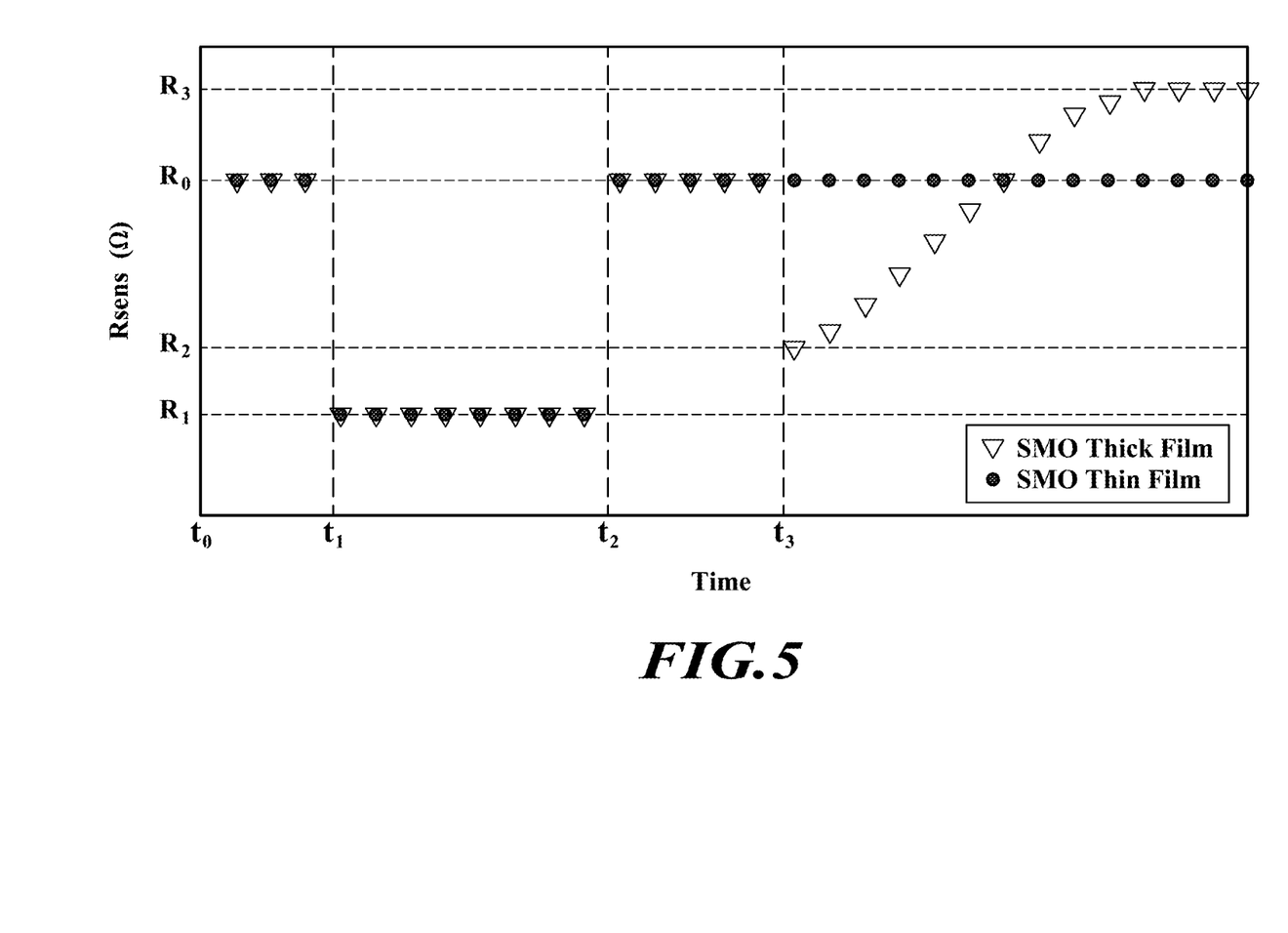
FIG. 5 is a chart showing resistances of the SMO thin film and the SMO thick film in response to being exposed to a VOC and a siloxane according to an embodiment of the present disclosure.

Due to these differences between the SMO thin film 16 and the SMO thick film 22 (e.g., the SMO thin film 16 being non-porous and the SMO thick film 22 being porous), the SMO thin film 16 and the SMO thick film 22 react differently to gases with large molecules, such as siloxanes. FIG. 5 is a chart showing resistances of the SMO thin film 16 and the SMO thick film 22 in response to being exposed to a VOC and a siloxane according to an embodiment of the present disclosure.

Between time $t_0$ and time $t_1$, the SMO thin film 16 and the SMO thick film 22 are both unexposed to a VOC and siloxane. As a result, the SMO thin film 16 and the SMO thick film 22 do not react with any gas molecules, and their resistances remain unchanged. The SMO thin film 16 and the SMO thick film 22 have an initial resistance $R_0$.

Between time $t_1$ and time $t_2$, the SMO thin film 16 and the SMO thick film 22 are both exposed to a VOC, such as ethanol, and react with the gas molecules of the VOC. As previously discussed with respect to FIGS. 3 and 4, the VOC molecules react with the SMO thin film's 16 exposed upper surface, and the VOC molecules react with the SMO thick film's 22 exposed upper surface and surfaces within the spaces 36 or cavities of the SMO thick film 22. As a result, the resistances of the SMO thin film 16 and the SMO thick film 22 undergo a change, and drop to a resistance $R_1$. It is noted that the SMO thin film 16 and the SMO thick film 22 react the same to the VOC and have the same resistance $R_1$ because, as previously discussed, the SMO thin film 16 and the SMO thick film 22 are made of the same material and are heated to the same temperature.

Between time $t_2$ and $t_3$, the VOC is released or vacated, and the SMO thin film 16 and the SMO thick film 22 are both once again unexposed to a VOC and siloxane. As a result, the SMO thin film 16 and the SMO thick film 22 do not react with any gas molecules, and return to the initial resistance $R_0$.

At time $t_3$, the SMO thin film 16 and the SMO thick film 22 are both exposed to a siloxane, such as cyclotrisiloxane (D3). In contrast to the exposure to the VOC between time $t_1$ and time $t_2$, the SMO thin film 16 and the SMO thick film 22 react differently to the siloxane at time $t_3$. Namely, the resistance of the SMO thin film 16 continues to remain at the initial resistance $R_0$, and the resistance of the SMO thick film 22 drops to the resistance $R_2$.

The SMO thin film 16 and the SMO thick film 22 each react differently to the siloxane due, at least in part, to the size of the siloxane molecules, and to the difference in porousness between the SMO thin film 16 and the SMO thick film 22. As previously discussed, the siloxane molecules react with the exposed upper surface of the SMO thin film 16 because the SMO thin film 16 is non-porous. The SMO thin film 16 undergoes very little, if any, change in resistance because the siloxane molecules are too large to react properly with the exposed upper surface. In contrast, as previously discussed, the siloxane molecules react with the exposed upper surface of the SMO thin film 16 and within the spaces 36 within the SMO thick film 22 because the SMO thick film 22 is porous. The SMO thick film 22 is able to react much more with the siloxane molecules compared to the SMO thin film 16 because the siloxane molecules react within the SMO thick film itself. As a result, the SMO thick film 22 will undergo a significant change in resistance.

It is noted that the resistance of the SMO thick film 22 may fluctuate when exposed to a siloxane. For example, as shown in FIG. 5, the SMO thick film 22 rises from the resistance $R_2$ to the resistance $R_3$, while being exposed to the siloxane. The resistance of the SMO thick film 22 may fluctuate for a variety of reasons. In some cases, for example, the resistance of the SMO thick film 22 fluctuates because the upper exposed surface of the SMO thick film 22, itself, is modified by the siloxane molecules such that the SMO thick film 22 is unable to maintain a steady resistance. For instance, the siloxane may modify the SMO thick film 22 such that the SMO thick film 22 is unable to maintain the resistance $R_2$. In other cases, for example, the resistance of the SMO thick film 22 fluctuates because the siloxane molecules become trapped or stuck within the SMO thick film 22 and hinder further chemical reactions.

As the SMO thin film 16 and the SMO thick film 22 react differently to siloxane, the SMO thin film 16 and the SMO thick film 22 can be used cooperatively to detect siloxanes or other similar gases with large molecules. Namely, the SMO thin film 16 and the SMO thick film 22 may be used simultaneously to gather data, and a siloxane may detected by comparing the offset or difference in resistances between the SMO thin film 16 and the SMO thick film 22. The detection of gases with large molecules, such as siloxanes, will be discussed in further detail with respect to FIG. 9.

Returning to FIG. 2, the heaters 18, 24 heat the SMO thin film 16 and the SMO thick film 22, respectively, to a desired temperature. In one embodiment, the heaters 18, 24 are resistive heaters that heat the SMO thin film 16 and the SMO thick film 22 using the Joule effect, by dissipating current through a resistance. As will be discussed in further detail with respect to FIGS. 6-7, the heaters 18, 24 underlie and heat the SMO thin film 16 and the SMO thick film 22, respectively.

As previously discussed, the SMO thin film 16 and the SMO thick film 22 should be heated to a specific temperature in order to react with a specific gas. In one embodiment, the heaters 18, 24 heat the SMO thin film 16 and the SMO thick film 22, respectively, to be within the same temperature range in order to sense the same gas.

The temperature sensors 20, 26 measure the current temperature of the SMO thin film 16 and the SMO thick film 22, respectively. The temperature sensors 20, 26 are positioned adjacent to the SMO thin film 16 and the SMO thick film 22, respectively, in order to obtain accurate measurements. As will be discussed in further detail below, the temperature sensors 20, 26 are used as a feedback control device for automatically adjusting the heaters 18, 24, respectively, to heat the SMO thin film 16 and the SMO thick film 22 to desired temperatures. For example, the temperature sensor 20 may measure a current temperature of the SMO thin film 16, and the heater 18 may adjust its temperature based on the current temperature of the SMO thin film 16.

The processor 15 is coupled to the thin film gas sensor 12 and the bulk film gas sensor 14. The processor 15 is configured to activate and deactivate each of the thin film gas sensor 12 and the bulk film gas sensor 14; measure current resistivity of the SMO thin film 16 and the SMO thick film 22; control the heaters 18, 24 to heat the SMO thin film 16 and the SMO thick film 22 to a particular temperature; and communicate with the temperature sensors 20, 26 to obtain current temperatures of the SMO thin film 16 and the SMO thick film 22. The processor 15 may be any type of controller, microprocessor, or application specific integrated circuit (ASIC) that communicates with and controls the thin film gas sensor 12 and the bulk film gas sensor 14. The processor may be in a same package as the gas sensors or may be a separate chip.

In one embodiment, the processor 15 reads the current temperatures of the SMO thin film 16 and the SMO thick film 22 via the temperature sensors 20, 26, respectively; and then controls the heaters 18, 24 based on the current temperature of the SMO thin film 16 and the SMO thick film 22, respectively. For example, the processor 15 may receive the current temperature of the SMO thin film 16 via the temperature sensor 20, and adjust the heater 18 to maintain a desired temperature (e.g., between 300 degrees Celsius and 350 degrees Celsius) of the SMO thin film 16. By adjusting the heaters 18, 24 to specific temperatures, the processor 15 is able to tune the thin film gas sensor 12 and the bulk film gas sensor 14, more specifically the SMO thin film 16 and the SMO thick film 22, to be sensitive to a particular gas. In one embodiment, the processor 15 adjusts the heaters 18, 24 to maintain the same temperature range such that the SMO thin film 16 and the SMO thick film 22 are sensitive to the same gas.

Figure 6:
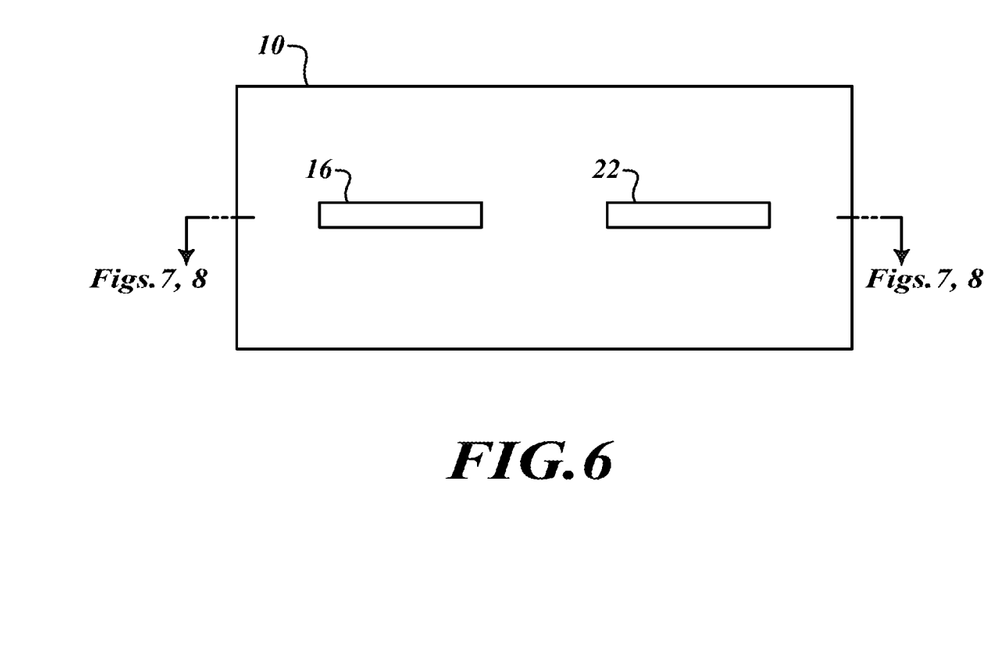
FIG. 6 is a top view of the gas sensor device according to an embodiment of the present disclosure.
Figure 7:
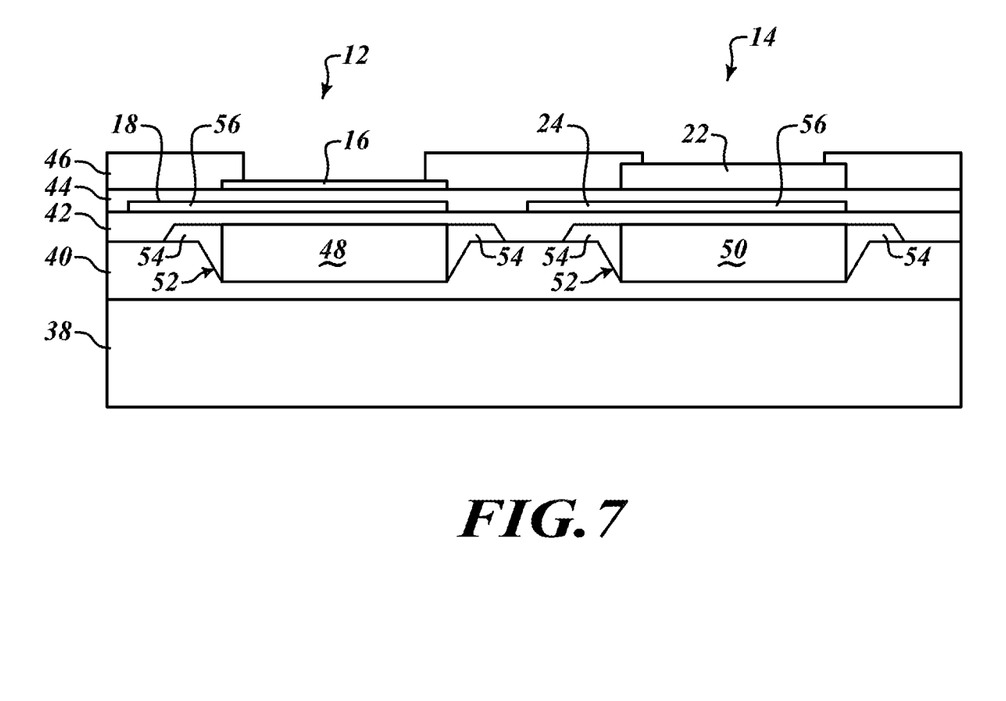
FIG. 7 is a cross-sectional view of the gas sensor device along the axis shown in FIG. 6 according to an embodiment of the present disclosure.

FIG. 6 is a top view of the gas sensor device 10 according to an embodiment of the present disclosure. FIG. 7 is a cross-sectional view of the gas sensor device 10 along the axis shown in FIG. 6 according to an embodiment of the present disclosure. It is beneficial to review FIGS. 6 to 7 together. It is noted that the dimensions set forth herein are provided as examples. Other dimensions are envisioned for this embodiment and all other embodiments of this application.

The gas sensor device 10 includes the SMO thin film 16 and the SMO thick film 22; the heaters 18, 24; a substrate 38; a first dielectric layer 40; a second dielectric layer 42; a third dielectric layer 44; and a fourth dielectric layer 46.

The first dielectric layer 40 is formed on the substrate 38 using, for example, deposition or a growth process. The substrate 38 may be made of, for example, silicon or glass. In one embodiment, the substrate 38 has a thickness in the range of 500 micrometers to 600 micrometers. The first dielectric layer 40 may be made of, for example, oxide. In one embodiment, the first dielectric layer 40 has a thickness in the range of 3 micrometers to 10 micrometers.

The second dielectric layer 42 is formed on the first dielectric layer 40 using, for example, deposition or a growth process. The second dielectric layer 42 may be made of, for example, silicon nitride. In one embodiment, the second dielectric layer 42 has a thickness in the range of 300 nanometers to 550 nanometers.

Cavities 48, 50 are formed between the first dielectric layer 40 and the second dielectric layer 42. As best shown in FIG. 7, the thin film gas sensor 12 and the bulk film gas sensor 14 each includes a respective cavity. Namely, the thin film gas sensor 12 includes the cavity 48, and the bulk film gas sensor 14 includes the cavity 50. The cavities 48, 50 may be formed by patterning recesses 52 in the first dielectric layer 40 using, for example, photolithography and etching techniques; and filling the recesses 52 with a sacrificial material 54, such as polyimide. The second dielectric layer 42 may then be formed on the first dielectric layer 40 and the sacrificial material 54. Portions of the sacrificial material 54 may then be removed using, for example, photolithography and etching techniques. Remaining portions of the sacrificial material 54, as best shown in FIG. 7, provide additional support for portions of the second dielectric layer 42 overlying the cavities 48, 50. In one embodiment, each of the cavities 48, 50 has a depth in the range of 2 micrometers to 5 micrometers.

The cavities 48, 50 provide air gaps between the first dielectric layer 40 and the second dielectric layer 42. As air has low thermal conductivity, the cavities 48, 50 provide thermal insulation and confine heat within the thin film gas sensor 12 and the bulk film gas sensor 14. As a result, temperatures of the SMO thin film 16 and the SMO thick film 22 may be maintained with less power. In addition, as polyimide also has low thermal conductivity, using polyimide for the sacrificial material 54 provides additional thermal insulation for the thin film gas sensor 12 and the bulk film gas sensor 14.

The heaters 18, 24 are formed on the second dielectric layer 42 using, for example, deposition. The heaters 18, 24 directly overlie the cavities 48, 50, respectively. As previously discussed, in one embodiment, the heaters 18, 24 are resistive heaters that heat the SMO thin film 16 and the SMO thick film 22 using the Joule effect by dissipating current through a resistance. In this embodiment, the heaters 18, 24 include a resistive layer 56, such as tantalum aluminum. In one embodiment, the resistive layer 56 has a thickness in the range of 100 nanometers to 200 nanometers. Although a single resistive layer is shown in FIG. 7, the heaters 18, 24 may include a plurality of resistive layers. In one embodiment, the heaters 18, 24 include at least one resistive layer on both sides of the SMO thin film 16 and the SMO thick film 22 such that at least a portion of the SMO thin film 16 and the SMO thick film 22 are sandwiched between two resistive layers.

The third dielectric layer 44 is formed on the second dielectric layer 42 and the heaters 18, 24 using, for example, deposition or a growth process. The third dielectric layer 44 may be made of, for example, silicon nitride. In one embodiment, the third dielectric layer 44 has a thickness in the range of 200 nanometers to 400 nanometers.

The SMO thin film 16 and the SMO thick film 22 are formed on the third dielectric layer 44 using, for example, deposition. The SMO thin film 16 and the SMO thick film 22 may be formed by forming an SMO layer on the third dielectric layer 44 and patterning the SMO layer using, for example, photolithography and etching techniques. As previously discussed, SMO thin film 16 and the SMO thick film 22 are made of a materials that chemically react with various gases in a surrounding environment. For example, the SMO thin film 16 and the SMO thick film 22 may include tin oxide ($SnO_2$), zinc oxide ($ZnO_2$), and/or indium oxide ($In_2O_3$). In one embodiment, the SMO thin film 16 has a thickness in the range of 50 nanometers to 150 nanometers. In one embodiment, the SMO thick film 22 has thickness in the range of 300 nanometers to 550 nanometers.

A fourth dielectric layer 46 is formed on the third dielectric layer 44 and the SMO thin film 16 and the SMO thick film 22 using, for example, deposition or a growth process. The fourth dielectric layer 46 is patterned using, for example, photolithography and etching techniques to expose the SMO thin film 16 and the SMO thick film 22 such that the SMO thin film 16 and the SMO thick film 22 are exposed to a surrounding environment, as shown in FIG. 7. The fourth dielectric layer 46 may be made of, for example, silicon nitride. In one embodiment, the fourth dielectric layer 46 has a thickness in the range of 300 nanometers to 550 nanometers.

In the embodiment shown in FIGS. 6 to 7, the thin film gas sensor 12 and the bulk film gas sensor 14 are both formed on the same die. Namely, the thin film gas sensor 12 and the bulk film gas sensor 14 are formed on the substrate 38. In another embodiment, the thin film gas sensor 12 and the bulk film gas sensor 14 are formed on separate dies.

It is noted that the processor 15 and the temperature sensors 20, 26 are not shown in FIGS. 6 to 7 for simplicity purposes. In one embodiment, the thin film gas sensor 12 and the bulk film gas sensor 14 and the processor 15 are all formed on the same substrate. In one embodiment, the processor 15 is formed on a separate substrate from the thin film gas sensor 12 and the bulk film gas sensor 14, and is electrically coupled to the thin film gas sensor 12 and the bulk film gas sensor 14 via an interconnect. In one embodiment, the temperature sensors 20, 26 are positioned adjacent to the SMO thin film 16 and the SMO thick film 22, respectively, in order to obtain accurate measurements. In addition, although not shown in FIGS. 6 to 7, the gas sensor device 10 may include a plurality of conductive layers that electrically couple the SMO thin film 16, the SMO thick film 22, and the heaters 18, 24 to the processor 15 and/or other electrical components (e.g., transistors, capacitors, resistors, etc.).

Figure 8:
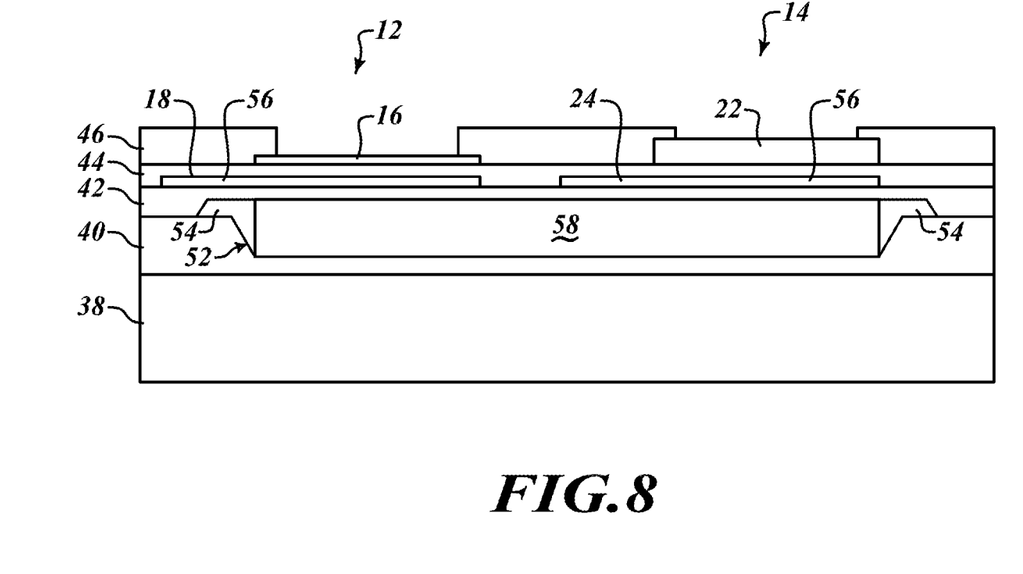
FIG. 8 is a cross-sectional view of the gas sensor device along the axis shown in FIG. 6 according to another embodiment of the present disclosure.

FIG. 8 is a cross-sectional view of the gas sensor device along the axis shown in FIG. 6 according to another embodiment of the present disclosure.

In the embodiment shown in FIG. 7, the thin film gas sensor 12 and the bulk film gas sensor 14 each includes a respective cavity. That is, the thin film gas sensor 12 includes the cavity 48, and the bulk film gas sensor 14 includes the cavity 50. In contrast, in the embodiment shown in FIG. 8, the thin film gas sensor 12 and the bulk film gas sensor 14 share a single cavity 58. Similar to the cavities 48, 50, the cavity 58 provides an air gap between the first dielectric layer 40 and the second dielectric layer 42 to provide thermal insulation for the thin film gas sensor 12 and the bulk film gas sensor 14. As a result, temperatures of the SMO thin film 16 and the SMO thick film 22 may be maintained with less power. By using the cavity 58 instead of the multiple cavities 48, 50, fabrication of the gas sensor device 10 is also simplified. In addition, the cavity 58 provides a larger air gap for increased thermal insulation.

As previously discussed, the SMO thin film 16 and the SMO thick film 22 react differently to siloxanes. The SMO thin film 16 will undergo very little, if any, change in resistance when exposed to a siloxane, and the SMO thick film 22 will undergo a significant change in resistance when exposed to a siloxane. Thus, siloxanes may be detected based on a variation between the resistances of the SMO thin film 16 and the SMO thick film 22.

Figure 9:
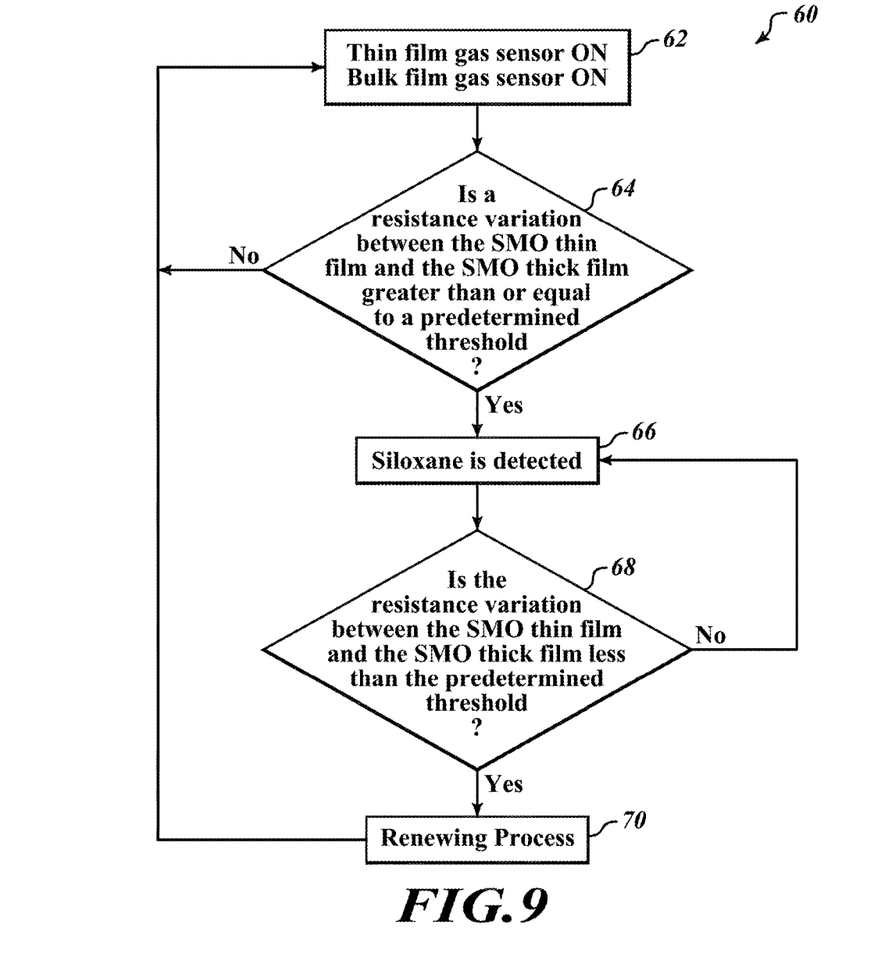
FIG. 9 is a flow diagram of a method of operating the gas sensor device for detecting a siloxane according to an embodiment of the present disclosure.

FIG. 9 is a flow diagram of a method 60 of operating the gas sensor device 10 for detecting a siloxane according to an embodiment of the present disclosure.

In block 62, the thin film gas sensor 12 is ON and the bulk film gas sensor 14 is ON. In particular, the processor 15 activates the thin film gas sensor 12 and the bulk film gas sensor 14 simultaneously. When the thin film gas sensor 12 and the bulk film gas sensor 14 are activated, the heaters 18, 24 are turned on to heat the SMO thin film 16 and the SMO thick film 22, respectively, to a desired temperature. In one embodiment, as previously discussed, the SMO thin film 16 and the SMO thick film 22 are heated to the same temperature. In addition, the processor 15 monitors the resistances of the SMO thin film 16 and the SMO thick film 22.

In decision branch 64, the processor 15 determines whether a resistance variation (Z) between the SMO thin film 16 and the SMO thick film 22 is greater than or equal to a predetermine threshold. For example, in decision branch 64, the processor 15 may determine whether the resistance variation (Z) is greater than 5%. It is noted that any predetermined threshold may be used.

In one embodiment, the resistance variation (Z) is determined using a reference ratio (CST) of the SMO thin film 16 and the SMO thick film 22, and a current ratio (VAR) of the SMO thin film 16 and the SMO thick film 22. The resistance variation (Z) may be calculated using equation (1):

$$Z = \frac{CST - VAR}{CST} \quad (1)$$

The reference ratio (CST) is a defined constant that is used as a reference value. The reference ratio (CST) is determined beforehand by exposing the SMO thin film 16 and the SMO thick film 22 to a selected gas, such as a VOC, having a known concentration range. The reference ratio (CST) is a ratio between (1) a change of resistance ($\Delta Rthin_{reference}$) of the SMO thin film 16 in response to a first change in gas concentration ($\Delta C_1$) of the selected gas, divided by the first change in gas concentration ($\Delta C_1$); and (2) a change of resistance of the SMO thick film 22 ($\Delta Rthick_{reference}$) in response to a second change in gas concentration ($\Delta C_2$) of the selected gas, divided by the second change in gas concentration ($\Delta C_2$). The reference ratio (CST) may be calculated using equation (2):

$$CST = \frac{\Delta Rthin_{reference}/\Delta C_1}{\Delta Rthick_{reference}/\Delta C_2} \quad (2)$$

In one embodiment, the first gas concentration range ($\Delta C_1$) is equal to the second gas concentration range ($\Delta C_2$).

The current ratio (VAR) is calculated similar to the reference ratio (CST), except that the current ratio (VAR) is calculated using currently measured resistances of the SMO thin film 16 and the SMO thick film 22. In particular, the current ratio (VAR) is a ratio between (1) a current change of resistance ($\Delta Rthin_{current}$) of the SMO thin film 16 divided by the first gas concentration range ($\Delta C_1$), and (2) a current change of resistance of the SMO thick film 22 ($\Delta Rthick_{current}$) divided by the second gas concentration range ($\Delta C_2$). The current ratio (VAR) may be calculated using equation (3):

$$VAR = \frac{\Delta Rthin_{current}/\Delta C_1}{\Delta Rthick_{current}/\Delta C_2} \quad (3)$$

As previously discussed, the current ratio (VAR) is compared to the reference ratio (CST) using equation (1) to determine the resistance variation (Z) between the SMO thin film 16 and the SMO thick film 22.

If the variation (Z) is less than the predetermined threshold, the processor 15 determines that a siloxane is not present, and the method 60 returns to step 62 to continue monitoring for siloxanes. If the variation (Z) is greater than or equal to the predetermined threshold, the method 60 moves to block 66.

In block 66, the processor 15 determines that siloxane is present. In one embodiment, when the processor 15 determines that siloxane is present, the gas sensor device 10 sounds an alarm to alert a user. The method 60 then moves to decision branch 68.

In decision branch 68, the processor 15 determines whether the resistance variation (Z) between the SMO thin film 16 and the SMO thick film 22 is less than the predetermine threshold. For example, in decision branch 68, the processor 15 may determine whether the resistance variation (Z) is less than 5%.

If the variation Z is greater than or equal to the predetermined threshold, siloxane is still present and the method 60 returns to block 66. If the variation Z is less than the predetermined threshold, the processor 15 determines that a siloxane is no longer present, and the method 60 moves to block 70.

In block 70, a renewing process is performed. As previously discussed, the SMO thick film 22 is porous and includes the spaces 36. Because siloxane molecules are much larger than VOC molecules, the siloxane molecules often become stuck within the spaces 36 of the SMO thick film 22 and are unable to release from the SMO thick film 22. The renewing process releases any siloxane molecules that are stuck within the SMO thick film 22. In one embodiment, the renewing process is a burning sequence that heats the SMO thick film 22 to a high temperature (e.g., between 600 degrees Celsius and 800 degrees Celsius) to input energy in to the SMO thick film 22 and cause siloxane molecules to release from the SMO thick film 22.

Once the renewing process is complete, the method 60 returns to block 62, where the gas sensor device 10 begins to monitor for siloxanes again. In one embodiment, the renewing process is also performed on the SMO thin film 16.

It is noted that, although the flow diagram of the method 60 shown in FIG. 9 is discussed with respect to detecting siloxanes, the method 60 may be used to detect other gases with large molecules (e.g., a gas with a molecular weight between 150 g/mol and 450 g/mol).

As discussed with respect to FIG. 9, the gas sensor device 10 may be operated to detect siloxanes based on a variation between the resistances of the SMO thin film 16 and the SMO thick film 22. However, the gas sensor device 10 may also be operated to detect a specific gas that does not have large molecules (e.g., a gas with a molecular weight that is less than 100 g/mol), such as a VOC. For example, the gas sensor device 10 may be operated to specifically detect ethanol. As previously discussed, the SMO thin film 16 and the SMO thick film 22 react the same to gases, such as VOCs, when the SMO thin film 16 and the SMO thick film 22 are made of the same material and are heated to the same temperature. Thus, a selected gas may be detected based on a lack of variation between the resistances of the SMO thin film 16 and the SMO thick film 22 (i.e., the resistances of the SMO thin film 16 and the SMO thick film 22 reacting the same).

Figure 10:
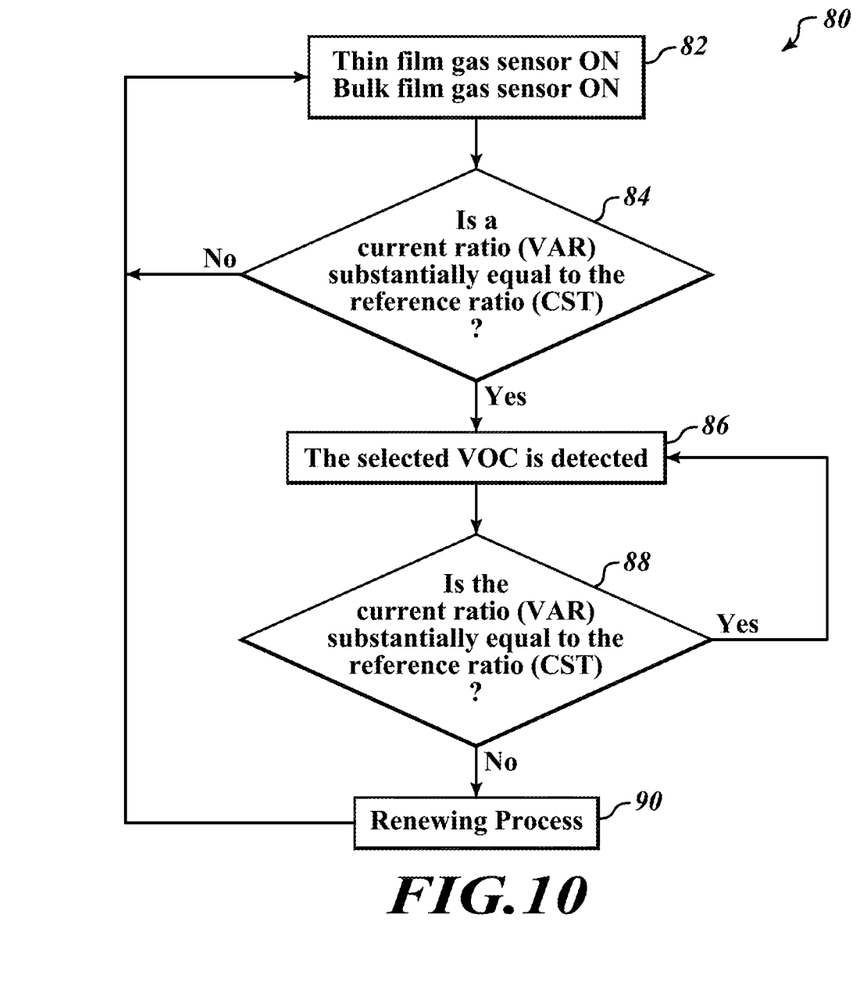
FIG. 10 is a flow diagram of a method of operating the gas sensor device for detecting a selected VOC according to an embodiment of the present disclosure.

FIG. 10 is a flow diagram of a method 80 of operating the gas sensor device 10 for detecting a selected VOC, such as ethanol, according to an embodiment of the present disclosure.

In block 82, similar to block 62 of the method 60, the thin film gas sensor 12 is ON and the bulk film gas sensor 14 is ON. In particular, the processor 15 activates the thin film gas sensor 12 and the bulk film gas sensor 14 simultaneously. When the thin film gas sensor 12 and the bulk film gas sensor 14 are activated, the heaters 18, 24 are turned on to heat the SMO thin film 16 and the SMO thick film 22, respectively, to a desired temperature. In one embodiment, as previously discussed, the SMO thin film 16 and the SMO thick film 22 are heated to the same temperature. In addition, the processor 15 monitors the resistances of the SMO thin film 16 and the SMO thick film 22.

In decision branch 84, the processor 15 determines whether the current ratio (VAR) of the SMO thin film 16 and the SMO thick film 22 is substantially equal to the reference ratio (CST) of the SMO thin film 16 and the SMO thick film 22.

As previously discussed, the reference ratio (CST) is a defined constant that is used as a reference value, and is determined beforehand using a selected gas having a known concentration range. The reference ratio (CST) is calculated using equation (2) above. For the embodiment of FIG. 10, the reference ratio (CST) is determined using the selected VOC.

As previously discussed, the current ratio (VAR) is calculated similar to the reference ratio (CST), except that the current ratio (VAR) is calculated using currently measured resistances of the SMO thin film 16 and the SMO thick film 22. The current ratio (VAR) is calculated using equation (3) above.

If the current ratio (VAR) is not substantially equal (e.g., greater than a 1% difference) to the reference ratio (CST), the processor 15 determines that the selected VOC is not present, and the method 80 returns to step 82 to continue monitoring for the selected VOC. If the current ratio (VAR) is substantially equal (e.g., less than a 1% difference) to the reference ratio (CST), the method 80 moves to block 86.

In block 86, the processor 15 determines that the selected VOC is present. In one embodiment, when the processor 15 determines that selected VOC is present, the gas sensor device 10 sounds an alarm to alert a user. The method 80 then moves to decision branch 88.

In decision branch 88, the processor 15 once again determines whether the current ratio (VAR) of the SMO thin film 16 and the SMO thick film 22 is substantially equal to the reference ratio (CST) of the SMO thin film 16 and the SMO thick film 22.

If the current ratio (VAR) is substantially equal (e.g., greater than a 1% difference) to the reference ratio (CST), the selected VOC is still present, and the method 80 returns to block 86. If the current ratio (VAR) is substantially equal (e.g., less than a 1% difference) to the reference ratio (CST), the processor 15 determines that the selected VOC is no longer present, and the method 80 moves to block 90.

In block 90, similar to block 70, a renewing process is performed. As previously discussed, the renewing process releases any molecules that are stuck within the SMO thick film 22. Once the renewing process is complete, the method 80 returns to block 82, where the gas sensor device 10 begins to monitor for the selected VOC again. In one embodiment, the renewing process is also performed on the SMO thin film 16.

It is noted that, although the flow diagram of the method 80 shown in FIG. 10 is discussed with respect to detecting a selected VOC, the method 80 may be used to detect other gases that do not have large molecules (e.g., a gas with a molecular weight that is less than 100 g/mol).

Figure 11:
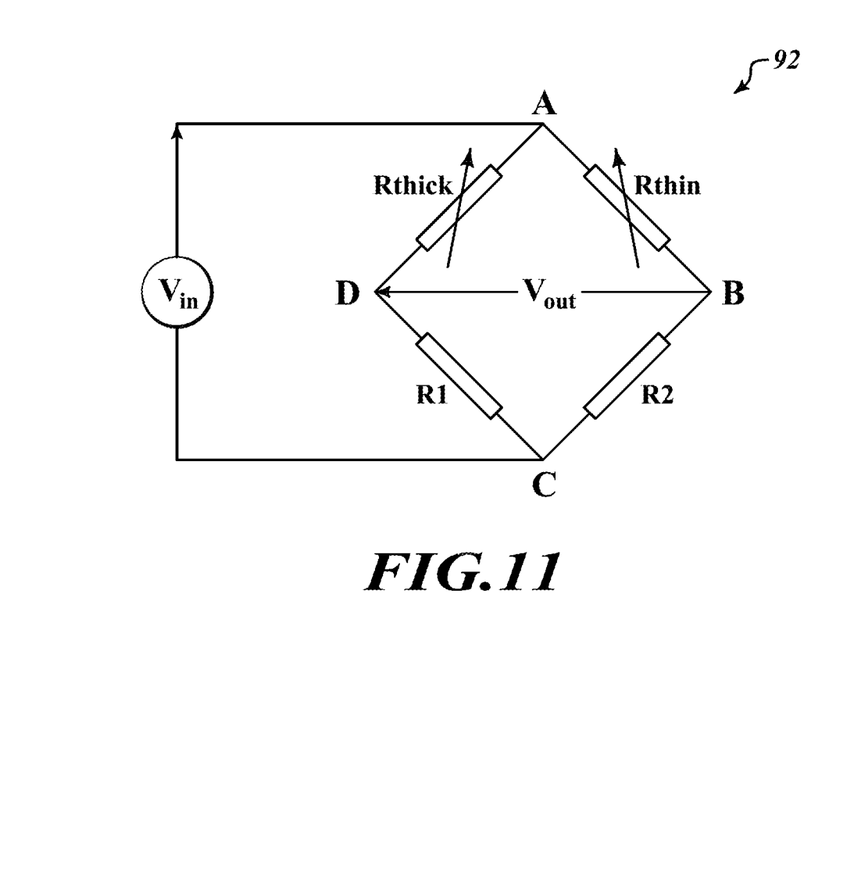
FIG. 11 is an electrical circuit to measure a variation between resistances of the SMO thin film and the SMO thick film according to an embodiment of the present disclosure.

FIG. 11 is an electrical circuit 92 to measure a variation between resistances of the SMO thin film 16 and the SMO thick film 22 according to an embodiment of the present disclosure.

The electrical circuit 92 includes the SMO thin film 16, represented by a resistor Rthin; the SMO thick film 22, represented by a resistor Rthick; and resistors R1, R2. The resistances of the resistor R1, R2 are known. The resistor Rthin, the resistor Rthick, and the resistors R1, R2 are arranged as a Wheatstone half bridge. In particular, the resistor Rthick is electrically coupled between nodes A and D, the resistor Rthin is electrically coupled between nodes A and B, the resistor R1 is electrically coupled between nodes D and C, and the resistor R2 is electrically coupled between nodes B and C.

As previously discussed, the SMO thin film 16 and the SMO thick film 22 reacts differently to siloxanes. The SMO thin film 16 will undergo very little, if any, change in resistance when exposed to a siloxane, and the SMO thick film 22 will undergo a significant change in resistance when exposed to a siloxane. As the resistance of the SMO thin film 16 will not change, the resistor Rthin may be used as a witness resistance in the Wheatstone bridge of the electrical circuit 92. That is, when an input voltage Vin is applied between nodes A and C, the output voltage Vout will be proportional to a change in resistance of the SMO thick film 22 (i.e., the resistor Rthick.

The various embodiments provide a gas sensor device that detects gases with large molecules, such as siloxanes. The gas sensor device may also be used to selectively detect other gases, such as VOCs.

The various embodiments described above can be combined to provide further embodiments. These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A method, comprising:
    activating a first gas sensor, the first gas sensor including a first semiconductor metal oxide (SMO) film having a first thickness;
    activating a second gas sensor, the second gas sensor including a second SMO film having a second thickness that is greater than the first thickness, the first gas sensor and the second gas sensor being activated concurrently; and
    detecting a gas based on the resistance of the first SMO film and the resistance of the second SMO film.

2. The method of claim 1, further comprising:
    sounding an alarm in response to a difference between the resistance of the first SMO film and the resistance of the second SMO film being greater than a threshold value.

3. The method of claim 1, further comprising:
    heating the second SMO film in response to a difference between the resistance of the first SMO film and the resistance of the second SMO film being less than a threshold value.

4. The method of claim 1 wherein the gas is a siloxane.

5. The method of claim 1 wherein the gas is a volatile organic compound (VOC).

6. A method, comprising:
    setting a thin film gas sensor and a bulk film gas sensor to an on state, the thin film gas sensor including a first semiconductor metal oxide (SMO) film having a first thickness, the bulk film gas sensor including a second SMO film having a second thickness greater than the first thickness; and
    detecting a gas based on resistances of the first SMO film and the second SMO film.

7. The method of claim 6 wherein the gas is a volatile organic compound (VOC).

8. The method of claim 6 wherein the detecting of the gas includes determining a ratio of the first SMO film and the second SMO film, the ratio of the first SMO film and the second SMO film is a ratio between (1) a change in resistance of the first SMO film divided by a first change in gas concentration and (2) a change in resistance of the second SMO film divided by a second change in gas concentration.

9. The method of claim 6 wherein the detecting of the gas includes:
    determining whether or not the ratio of the first SMO film and the second SMO film is substantially equal to a reference ratio; and
    detecting the gas in response to determining the ratio of the first SMO film and the second SMO film is substantially equal to the reference ratio.

10. The method of claim 9, further comprising:
    determining, subsequent to detecting the gas, whether or not the ratio of the first SMO film and the second SMO film is substantially different from the reference ratio;
    performing a renewing process in response determining the ratio of the first SMO film and the second SMO film is substantially different from the reference ratio.

11. The method of claim 10 wherein the renewing process includes heating the second SMO film.

12. A method, comprising:
    setting a first gas sensor to an on state by heating a first semiconductor metal oxide (SMO) film of the first gas sensor, the first SMO film having a first thickness;
    setting a second gas sensor to an on state by heating a second SMO film of the second gas sensor, the second SMO film having a second thickness greater than the first thickness; and
    detecting a presence of a gas based on resistances of the first SMO and the second SMO.

13. The method of claim 12 wherein the first SMO film and the second SMO film are heated to approximately the same temperature.

14. The method of claim 12 wherein the detecting of the presence of the gas includes detecting the gas based on a reference ratio and a ratio of the first SMO film and the second SMO film.

15. The method of claim 14 wherein the ratio of the first SMO film and the second SMO film is a ratio between (1) a change in resistance of the first SMO film divided by a first change in gas concentration and (2) a change in resistance of the second SMO film divided by a second change in gas concentration.

16. The method of claim 12 wherein the detecting of the presence of the gas includes:
    detecting the gas based on a resistance variation between the first SMO film and the second SMO film;
    determining whether or not the resistance variation is greater than or equal to a threshold value; and
    detecting the gas in response to determining the resistance variation is greater than or equal to the threshold value.

17. The method of claim 16, further comprising:
    determining, subsequent to detecting the gas, whether the resistance variation is less than the threshold value; and
    performing a renewing process in response determining the resistance variation is less than the threshold value.

18. The method of claim 17 wherein the renewing process includes heating the second SMO film.

19. The method of claim 12 wherein the gas is a siloxane.

20. The method of claim 12 wherein the gas is a volatile organic compound.

* * * * *